United States Patent [19]

Nordan

[11] Patent Number: 5,507,759
[45] Date of Patent: Apr. 16, 1996

[54] VARIABLE RESECTION KERATOPLASTY METHOD

[76] Inventor: Lee T. Nordan, 9834 Genesee Ave., Ste. 209, La Jolla, Calif. 92037

[21] Appl. No.: 180,964

[22] Filed: Jan. 14, 1994

[51] Int. Cl.$^6$ .................................................. A61B 17/32
[52] U.S. Cl. ............................................................ 606/166
[58] Field of Search ................................ 606/166, 5, 172

[56] References Cited

U.S. PATENT DOCUMENTS

| | | | |
|---|---|---|---|
| 4,173,980 | 11/1979 | Curtin | 606/166 |
| 4,298,004 | 11/1981 | Schachar et al. | 606/166 |
| 4,423,728 | 1/1984 | Lieberman | 606/166 |
| 4,662,370 | 5/1987 | Hoffmann et al. | 606/166 |
| 4,840,175 | 6/1989 | Peyman | 606/5 |
| 5,139,518 | 8/1992 | White | 606/166 X |
| 5,215,104 | 6/1993 | Steinert | 606/166 X |
| 5,288,292 | 2/1994 | Giraud et al. | 606/166 |
| 5,318,046 | 6/1994 | Rozakis | 606/166 X |

OTHER PUBLICATIONS

In–Situ Microkeratome Set brochure.
Kristine Morrill, Not–Stitch Microkeratome Technique Lauded, Jul. 15, 1992.

*Primary Examiner*—Michael H. Thaler
*Attorney, Agent, or Firm*—Henri J. A. Charmasson; John D. Buchaca

[57] ABSTRACT

A process for correcting the focusing aberrance of a patient's eye by sectioning one or more lamellar portions off the external surface of the cornea to either increase or decrease the external curvature of the cornea to an extent sufficient to correct said aberrance. A stabilizing vacuum ring is first placed against the cornea and around the area to be sectioned, a pressure plate presses a portion of the ordinarily curved surface of the cornea to be flat, then a blade is translated across the opening of the ring while the height of the pressure plate is varied. The resulting sinuous path of the blade through the corneal material cuts a section of varying thickness. A set of elliptical cams adjusts the height of the plate in relation to the ring during the translating movement. The cams determine the depth of the resection, and the radius of curvature along the sinuous path. The resected portions of the cornea are discarded. The simplified process requires only the natural regrowth of the epithelium over the resected area to complete the surgery.

2 Claims, 2 Drawing Sheets

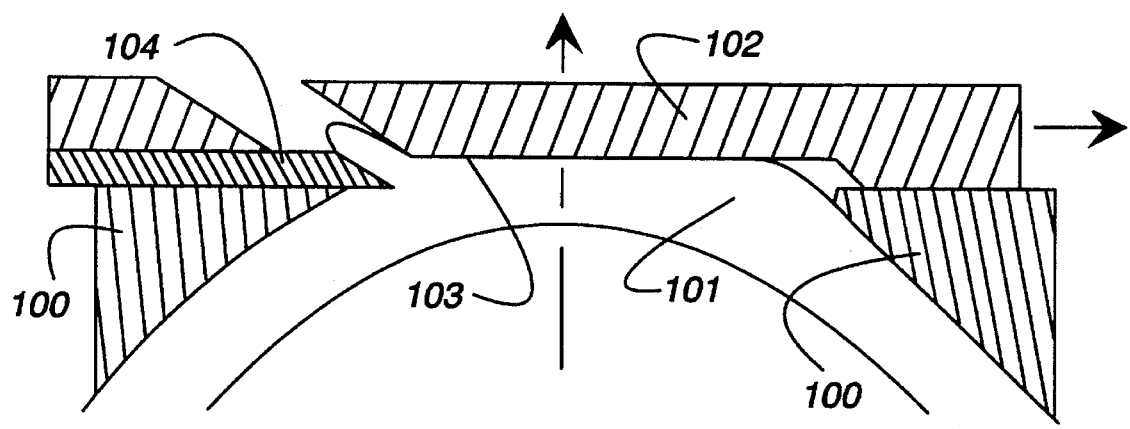
FIG 1A, PRIOR ART
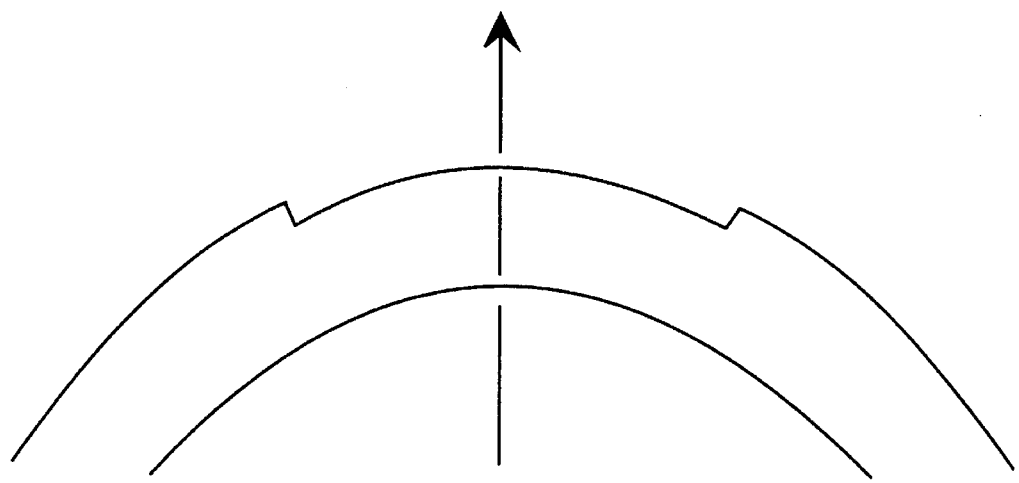
FIG 1B, PRIOR ART 5,507,759

VARIABLE RESECTION KERATOPLASTY METHOD

FIELD OF THE INVENTION

This invention relates to ophthalmic surgical procedure, and more specifically to procedures which modify the curvature of the cornea such as keratomileusis and other forms of refractive and lamellar keratoplasty.

BACKGROUND OF THE INVENTION

Common forms of refractive surgery include radial keratotomy in which a series of micro-incisions are made radially on the anterior surface of the cornea in order to modify its curvature, photo-reactive keratoplasty in which the surface of the cornea is flattened or steepened using an ablating laser beam, keratomileusis in which a lamellar portion of the cornea is removed and discarded or removed then reinstalled after reshaping its recipient bed and/or reshaping the portion itself by further lamellar resection. Each one of the above-mentioned procedures comprises a multi-step operation and suffers from a limited degree of precision.

In keratomileusis the lamellar cap is usually removed by means of a special scalpel such as the one available from Steinway Instrument Company Inc. of San Diego, Calif. under the brand name MICROKERATOME. This instrument comprises a stabilizing ring 100 which is held by vacuum against the cornea 101 and around the area to be resected, a plate 102 situated atop the ring which contacts the portion of cornea poking through the ring thereby flattening it 103 and securing its position at a specified height within the ring, and a blade 104 that can be translated linearly across the aperture of the ring. Accordingly, the cuts made by this instrument are not by themselves corrective since the section is of uniform thickness as shown in FIG. 1B. Either the sectioned bed or the sectioned cap must still be reshaped. In the case of myopia, a second smaller diameter section is taken from the bed, then the first section replaced. In the case of hyperopia, the first section is discarded, allowing the healing cornea to form a steepened surface. It would be advantageous to be able to modify the surface of the cornea in a single sectioning step, thereby reducing the time needed to perform the sergery and the time required to heal.

SUMMARY OF THE INVENTION

The principal and secondary objects of the present invention are to provide a simplified type of refractive surgery by modifying the curvature of the anterior surface of the cornea in a single sectioning step.

These and other objects are achieved by altering the height of the corneal pressure plate as it and the sectioning blade are translated across the cornea. After the apparatus is removed, the resilient cornea returns to its natural shape, minus the section. The resultant topography of the corneal surface corrects the prior condition. In the preferred embodiment of an apparatus for implementing this process, the plate height is accurately controlled by a set of elliptical cams. As the plate height changes, the compression of the surface of the cornea changes. This changes the depth of penetration of the blade into the cornea, resulting in a sinuous path for the blade relative to the original surface of the cornea. However, the height of the blade in relation to the base ring placed around the cornea remains constant.

BRIEF DESCRIPTION OF THE DRAWING

FIG. 1A is a cross-sectional view of the prior art apparatus sectioning the surface of a cornea;

FIG. 1B is a cross-sectional view of a cornea after a section of uniform thickness is removed using the prior art process of FIG. 1A;

DESCRIPTION OF THE PREFERRED EMBODIMENT OF THE INVENTION

Figure 1:
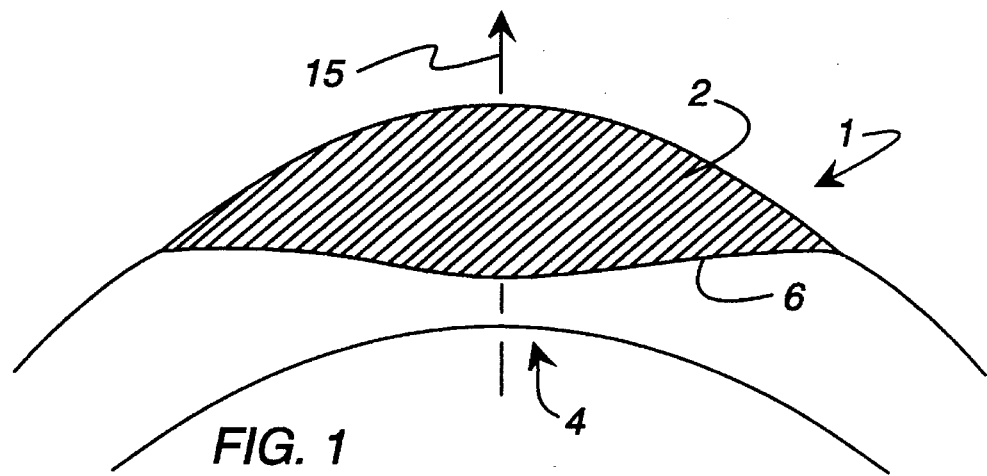
FIG. 1 is a diagrammatical illustration of an exemplary surgical resection for the correction of myopia.
Figure 2:
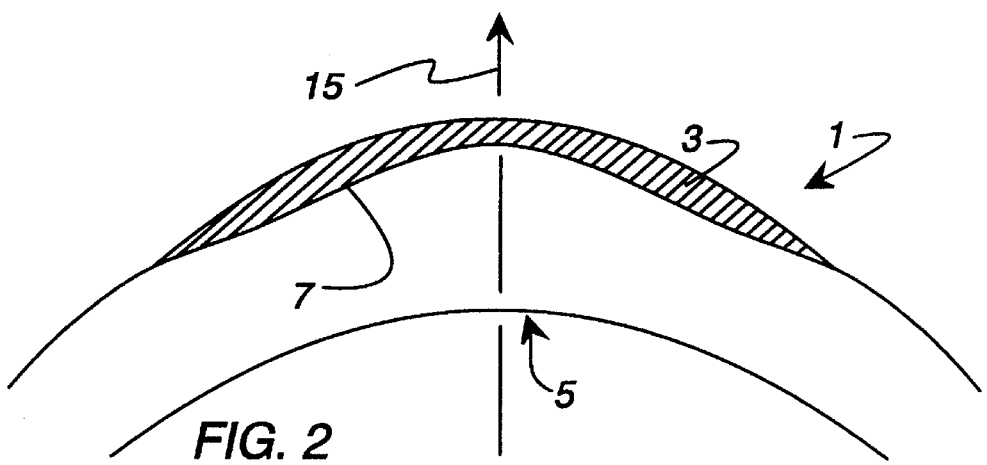
FIG. 2 is a diagrammatical illustration of an exemplary surgical resection for the correction of hyperopia.
Figure 3:
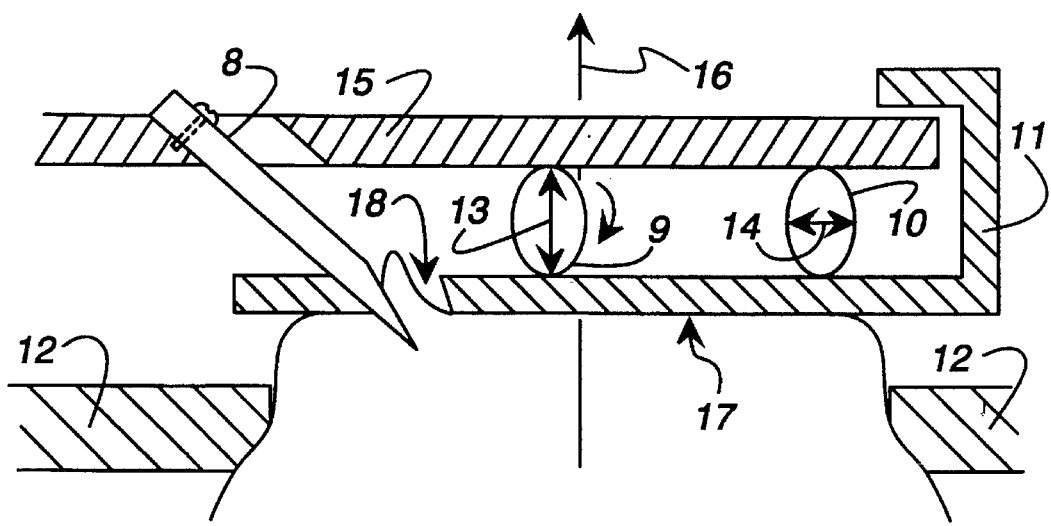
FIG. 3 is a diagrammatical illustration of a cutting blade mechanical control system.

Referring now to the drawing, the basic principle of the invention will be disclosed with reference to FIGS. 1–3. The invention process is concerned essentially with the reshaping of the outer surface 1 of the cornea of a patient eye in order to either, increase its radius of curvature and thus correct myopia, or decrease said radius and thus correct hyperopia. The correction of any such aberrance is accomplished in a single resective operation whereby a lamellar cap 2, 3 is removed and discarded, leaving a reshaped central area 4, 5 of the cornea over which the epithelium is allowed to regrow.

In order to achieve the desired correction, the resection must be made along a defined sinuous cutting path 6, 7 characterized by one or more degrees and directions of curvature. Although the instant process requires a corneal resection as in other refractive surgery processes such as keratomileusis or refractive or lamellar keratoplasty, the necessity of adjusting the resecting direction along a precise non-linear path calls for special instrumentation.

As stated in the Background section, the instrument used to cut a corneal cap in the prior art keratomeleusis process, such as those sold under the name MICROKERATOME by Steinway Instruments, Inc. of San Diego, Calif., comprises a blade mounted within a pressure plate that can be translated across the opening of a base ring that is secured by vacuum against the patient's cornea and around the central outer portion of it to be sectioned. The substantially planar plate compresses a normally curved portion of the outer surface of the cornea into a substantially flat surface. The blade and plate combination traverses linearly and parallel to the plane in which the base ring lies, i.e., always perpendicular to the axis of vision. Since the pressure provided by the plate is constant and the depth of the blade within the corneal material does not change, the resulting lamellar section is of constant thickness.

The invention may be practiced by using a modified version of the MICROKERATOME device in which the blade 8 is mounted on a structure or carriage 15 separate from the plate 11 which has a substantially planar undersurface 17. The blade extends through an aperture 18 in the plate much like a carpenter's plane. Although the carriage and blade combination follow a linear path perpendicular to the axis of vision 16, the height or position of the pressure plate 11 with respect to the carriage 15 and ring 12 is allowed to vary. This height is controlled by one or more eccentric cams 9, 10 separating the carriage from the pressure plate. These cams adjust the height of the plate as a function of the blade's lateral position, i.e. how far it has traversed across the surface of the cornea.

The shape and size of the cams determine the type and degree of correction that will be achieved. For example, an ellipsoidal set of cams 9, 10 may be used for correcting myopic or hyperopic aberrance. In the first case where the outer curvature of the cornea must be decreased, the resection must be progressively increased as the blade advances toward the axis of vision. Accordingly, the cams 9, 10 must be positioned such that their longest diameters 13 control the depth of the blade at the beginning and end of the sectioning process. In other words, as the shortest diameters 14 of the cams is positioned between the blade carriage 15 and the pressure plate 11, the blade must then be crossing over the axis of vision 16 where the removed lamellar cap 2 has to reach its greatest thickness in the case of myopia. Hyperopia may be corrected by starting the resection when the shortest diameters 14 of the cams separate the blade carriage 15 from the pressure plate 11 in order to achieve the most shallow cut as the blade crosses over the apex of the cornea at the axis of vision, 16, i.e., as the pressure on the cornea and thus the resultant cutting depth is determined by the longest diameters of the cams. It should be understood that the outer profiles and the sizes of the cams can be modified to achieve an infinite variety of resecting paths as may be required to obtain the desired visual correction.

Instead of using eliptical rollers to adjust the height of the carriage with respect to the vacuum ring, any number of other equivalent mechanisms may be used, such as vertical cams extending from the carriage and engaging an aperture of varying width in the plate, a vertical prong engaging a trough of varying depth much like the stylus of a record player, and miniature electronic servos with robotic control.

All of these mechanisms would still use the inventive process described above.

While the preferred embodiments of the invention have been described, modifications can be made and other embodiments may be devised without departing from the spirit of the invention and the scope of the appended claims.

What is claimed is:

1. A surgical process for correcting the focusing aberrance of a patient eye, which comprises:

removing a lamellar cap off the cornea of said eye by sectioning a central, anterior portion of said cornea along a sinuous path;

wherein said sectioning comprises:

selecting at least one radius and at least one radial direction of curvature for said sinuous path in order to modify the curvature of said anterior portion to a degree sufficient to correct said aberrance; and driving a sectioning blade along said sinuous path;

wherein said driving comprises:

placing a stabilizing ring against said cornea and around said anterior portion;

pressing a pressure plate against said cornea and around said anterior portion; and controlling the position of said plate in relation to said ring by means of an eccentric cam.

2. The process of claim 1, wherein said controlling comprises using at least one cam having an elliptic profile.

* * * * *